(12) United States Patent
Johnson et al.

(10) Patent No.: US 6,569,118 B2
(45) Date of Patent: May 27, 2003

(54) ADAPTER AND METHOD OF ATTACHMENT FOR "LUER LOK" RECEPTACLES

(75) Inventors: Johnnie M. Johnson, 1281 Sunset Cliffs Blvd., San Diego, CA (US) 92107; Marc Pilkington, San Diego, CA (US)

(73) Assignee: Johnnie M. Johnson, San Diego, CA (US)

( * ) Notice: Subject to any disclaimer, the term of this patent is extended or adjusted under 35 U.S.C. 154(b) by 0 days.

(21) Appl. No.: 09/866,176

(22) Filed: May 25, 2001

(65) Prior Publication Data

US 2002/0010433 A1 Jan. 24, 2002

Related U.S. Application Data

(60) Provisional application No. 60/241,442, filed on Oct. 19, 2000, provisional application No. 60/241,156, filed on Oct. 18, 2000, and provisional application No. 60/206,799, filed on May 25, 2000.

(51) Int. Cl.[7] .............................................. A61M 5/178
(52) U.S. Cl. .................... 604/164.04; 604/181; 604/264
(58) Field of Search .................... 604/27, 48, 93.01, 604/104, 115, 164.01, 164.03, 164.04, 164.1, 164.11, 164.12, 181, 264

(56) References Cited

U.S. PATENT DOCUMENTS

| | | | |
|---|---|---|---|
| 3,648,927 A | | 3/1972 | Abbe et al. |
| 4,220,151 A | * | 9/1980 | Whitney .................... 604/110 |
| 4,294,250 A | * | 10/1981 | Dennehey .................... 604/403 |
| 4,607,868 A | * | 8/1986 | Harvey et al. ................. 285/12 |
| 4,981,469 A | * | 1/1991 | Whitehouse et al. ........ 604/535 |
| 5,002,538 A | | 3/1991 | Johnson |
| 5,478,328 A | * | 12/1995 | Silverman et al. .......... 604/110 |
| 5,533,708 A | * | 7/1996 | Atkinson et al. ......... 251/149.1 |
| 5,555,908 A | * | 9/1996 | Edwards et al. .......... 137/329.1 |
| 5,591,138 A | * | 1/1997 | Vaillancourt ................ 604/192 |
| 5,620,427 A | * | 4/1997 | Werschmidt et al. .... 137/516.13 |
| 5,651,776 A | * | 7/1997 | Appling et al. .............. 285/332 |
| 5,807,345 A | * | 9/1998 | Grabenkort .................. 215/211 |
| 5,830,195 A | * | 11/1998 | Peters et al. ................. 604/533 |
| 6,217,564 B1 | * | 4/2001 | Peters et al. ................. 604/111 |
| 6,280,418 B1 | * | 8/2001 | Reinhard et al. ............ 604/181 |
| 6,290,688 B1 | * | 9/2001 | Lopez et al. ................. 604/500 |
| 6,394,983 B1 | * | 5/2002 | Mayoral et al. ............. 604/192 |

OTHER PUBLICATIONS

Red Line Health Care, NEEDLES, sales brochure, p. 194.
Engineers EXPRESS, FEMALE LUER, sales brochure, p. 34.
TULIP SUPERLUERLOK, Tulip Medical, advertising brochure, 2000.

* cited by examiner

Primary Examiner—Ira S. Lazarus
Assistant Examiner—Andrea M. Ragonese
(74) Attorney, Agent, or Firm—Stephen A. Gratton

(57) ABSTRACT

An adapter for a "LUER LOK" receptacle includes a housing having an internal recess configured to engage a hub of the receptacle. The adapter also includes a fitting attached to the housing, and to a medical instrument such as a cannula or a needle. The fitting includes a tapered recess configured to engage a tapered post of the receptacle. The fitting also includes a male end portion configured to engage female threads on the hub of the receptacle. The male end portion can include threads or alternately a flange. The adapter strengthens and rigidifies the receptacle, and allows the medical instrument to be aggressively manipulated, with less chance of damage to the receptacle and fluid leakage therefrom. In an alternate embodiment adapter, the tapered post of the receptacle is removed to provide an enlarged opening for the receptacle. The enlarged opening permits fluids, tissue and cells to be transferred with less damage and less resistance. A method for attaching the medical instrument to the receptacle includes the steps of: providing the adapter with the medical instrument, then attaching the adapter to the receptacle using aligning, pressing and twisting steps.

30 Claims, 4 Drawing Sheets

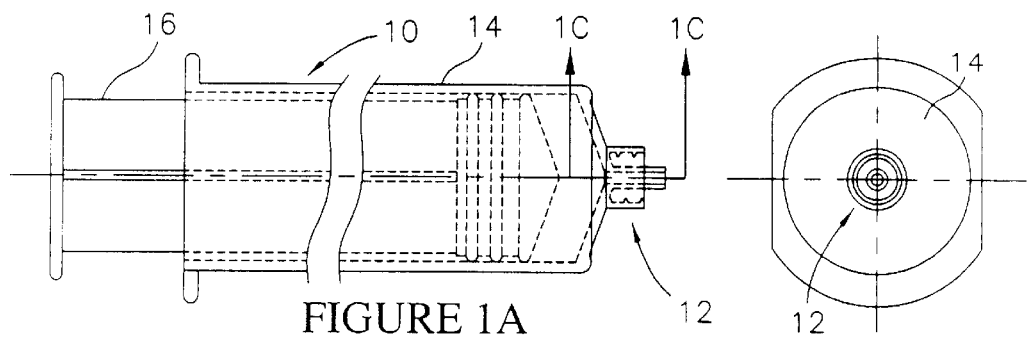
FIGURE 1A
(PRIOR ART)
FIGURE 1B
(PRIOR ART)
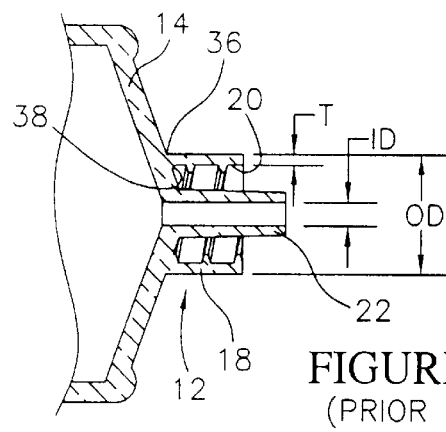
FIGURE 1C
(PRIOR ART)
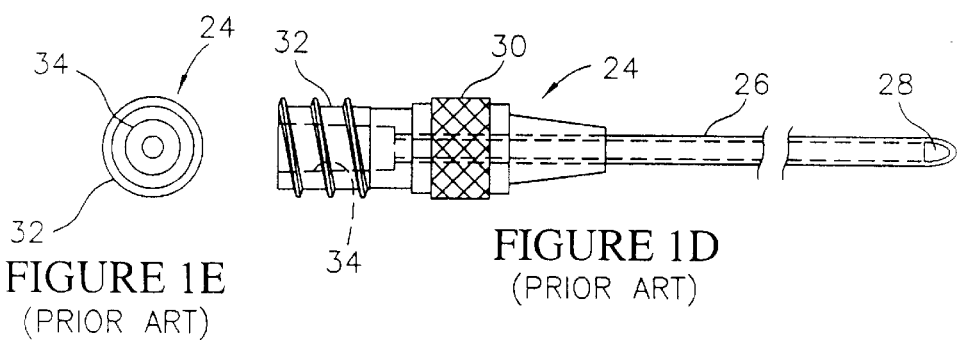
FIGURE 1E
(PRIOR ART)
FIGURE 1D
(PRIOR ART)
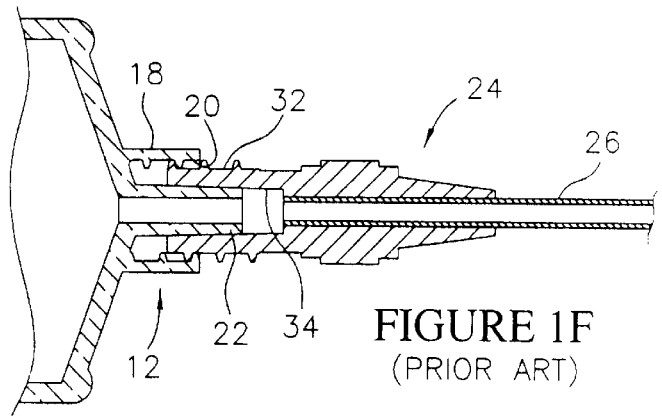
FIGURE 1F
(PRIOR ART)

ADAPTER AND METHOD OF ATTACHMENT FOR "LUER LOK" RECEPTACLES

CROSS REFERENCE TO RELATED APPLICATIONS

This application claims the benefit of U.S. Provisional Application No. 60/206,799 filed May 25, 2000, of U.S. Provisional Application No. 60/241,156 filed Oct. 18, 2000 and of U.S. Provisional Application No. 60/241,442 filed Oct. 19, 2000.

FIELD OF THE INVENTION

This invention relates generally to medical equipment, and more particularly to an adapter for "LUER LOK" receptacles, and to a method of attachment to "LUER LOK" receptacles.

BACKGROUND OF THE INVENTION

One well known receptacle used to connect and establish fluid communication between different medical components is known as a "LUER LOK". "LUER LOK" receptacles are widely used to connect syringes to medical instruments, such as needles and cannulas, and to connect medical conduits to one another. In addition, "LUER LOK" receptacles have a standard configuration that allows different sizes and types of instruments to be connected to the same receptacle.

Referring to FIGS. 1A–1F, a syringe 10 that includes a "LUER LOK" receptacle 12 is illustrated. As shown in FIGS. 1A and 1B, the syringe 10 includes a barrel 14, and a plunger 16 configured to push a liquid or viscous fluid through the receptacle 12 and out of or into the barrel 14. As shown in FIG. 1C, the receptacle 12 includes a cylindrical hub 18 having an outside diameter with a finished surface, and an inside diameter threaded with double lead female threads 20. The hub 18 is sometimes referred to as the "female" portion of the receptacle 12.

The receptacle 12 also includes a tapered post 22 located partially within the hub 18 but which extends outside of the confines of the hub 18. As with the outside diameter of the hub 18 the outside surface of the tapered post 22 is also smooth. The tapered post 22 is sometimes referred to as the "male" portion of the receptacle 12, and is sometimes referred to as a "LUER" tapered coupling. Typically, the hub 18, the tapered post 22, and the barrel 14, all comprise a same plastic material, which is molded into a unitary structure using an injection molding process.

Referring to FIGS. 1E and 1D, a cannula 24 configured for attachment to the receptacle 12 is illustrated. The cannula 24 includes a hollow cylindrical tip portion 26 on its distal end. The tip portion 26 includes an inside diameter which provides a fluid conduit, and a sharpened post 28 in fluid communication with the inside diameter. The cannula 24 also includes a knurled portion 30, and a threaded or flanged male portion 32 formed on an outside diameter thereof on its proximal end. In addition, the cannula 24 includes a tapered opening 34 in fluid communication with the inside diameter of the tip portion 26, and with the sharpened post 28. The tapered opening 34 is configured for mating engagement with the tapered post 22 of the receptacle 12.

Referring to FIG. 1F, the cannula 24 is shown attached to the receptacle 12. For attaching the cannula 24 to the receptacle 12, the tapered post 22 of the receptacle 12 is placed into the tapered opening 34 of the cannula 24. The mating configurations of the tapered post 22 and the tapered opening 34 forms a fluid tight seal therebetween. At the same time, the cannula 24 is twisted in a clock wise direction, so that the male threads 32 on its outside diameter, threadably engage the female threads 20 on the inside diameter of the hub 18. This twisting motion also "locks" the cannula 24 to the receptacle 12, and forms another fluid tight seal between the male threads 32 and the female threads 20.

This conventional "LUER LOK" receptacle 12 is used effectively throughout the world, but still has several disadvantages. One disadvantage is that the receptacle 12 is prone to crack and break, particularly at the intersection 36 (FIG. 1C) of the hub 18 with the syringe barrel 14, and at the intersection 38 of the tapered post 22 with the syringe barrel 14. This cracking and breaking compromises the strength of the mechanical connection between the receptacle 12 and the cannula 24, and compromises the fluid tight seals between the receptacle 12 and the cannula 24. Fluids leaking from the syringe 14 are a particular problem as they can adversely affect a medical procedure, and also present a biological hazard to patients and medical personnel.

This situation is compounded by cannulas, or other instruments, which are relatively long, or which require aggressive manipulation by medical personnel. For example, harvesting of tissue and cells from different organs of the body, requires relatively long cannulas and aggressive manipulation by physicians, which can damage the receptacle 12. In addition, the twisting motion required to lock the cannula 24 to the receptacle 12, can cause the hub 18 to expand outwardly during engagement of the male threads 32 on the cannula 24 with the female threads 20 on the receptacle 12. This expansion can also cause cracking and breaking to occur, or can cause micro cracks that lead to cracking and breaking.

Another disadvantage of the conventional "LUER LOK" receptacle 12 is that the inside diameter (ID-FIG. 1C) of the tapered post 22 is relatively small. Typically this inside diameter (ID-FIG. 1C) is only about 1.9–2.0 mm in size. An opening this small can cause problems for some medical procedures. For example, with harvesting of tissue and cells from the body, it is advantageous to treat the harvested material as gently as possible, in order to minimize damage and trauma. With a relatively small inside diameter (ID-FIG. 1C) the harvested material is squeezed into a relatively small area which can damage the material. Also, the relatively small diameter column of fluid moving through the inside diameter (ID-FIG. 1C) means a large percentage of the harvested material can be damaged by contact with the inside diameter (ID-FIG. 1C) of the tapered post 22.

The present invention is directed to an adapter for "LUER LOK" receptacles which functions to strengthen, to rigidify, to prevent spreading, and to prevent cracking of the receptacle. In addition, the adapter can be used to increase the inside diameter of the receptacle, such that medical fluids and/or harvested cells and tissue, can be more effectively processed.

SUMMARY OF THE INVENTION

In accordance with the present invention, an adapter for a "LUER LOK" receptacle, and a method for attaching a medical instrument to the receptacle, are provided.

The "LUER LOK" receptacle can be molded on a first medical instrument, such as a syringe, substantially as previously described. The receptacle includes a cylindrical hub having a smooth outside diameter, and a threaded inside diameter having female threads. The receptacle also includes a tapered post located partially within the hub, but extending outside of the confines of the hub.

The adapter is configured for attachment to the receptacle, and functions to strengthen and rigidify the receptacle. The adapter includes a generally cylindrical housing, which preferably comprises a rigid material such as metal, hard plastic or a composite. The housing includes a cylindrical recess configured to slip over the outside diameter of the hub on the receptacle. The inside diameter of the recess is sized relative to the outside diameter of the hub to provide a press fit, and also to seal the mating surfaces. Alternately, rather than a press fit, the inside diameter of the recess can be threaded with cutting threads adapted to cut mating threads on the outside diameter of the hub.

The adapter also includes a fitting which is attached to the housing, and to a second medical instrument, such as a cannula or a needle, having an internal conduit. The fitting includes an internal conduit in flow communication with the internal conduit on the second medical instrument. The fitting also includes a male end portion located within the recess, configured to engage the female threads on the hub of the receptacle. The male end portion can include male threads on an outside diameter thereof configured to threadably engage the female threads on the hub. Alternately the male end portion can have a flange, termed herein as a "butterfly", which is configured to engage the female threads on the hub. The fitting also includes a tapered recess in the male end portion configured to slip over the tapered post on the receptacle. As with the recess in the housing, the tapered recess is sized relative to the tapered post to provide a press fit, and also to seal the mating surfaces.

For attaching the adapter to the receptacle, the recess on the housing of the adapter is slid onto the hub on the receptacle (or alternately threaded onto the hub in the threaded embodiment). At the same time, the tapered post on the receptacle is slid into the tapered recess on the fitting of the adapter. The housing of the adapter is then twisted, such that the male end portion on the fitting engages the female threads on the hub. As thus attached, the recess in the housing encircles the hub on the receptacle to rigidify and prevent spreading of the hub. In addition, a first fluid tight seal is formed between the male end portion on the fitting and the female threads on the hub, a second fluid tight seal is formed between the tapered post and the tapered recess, and a rigidifying seal is formed between the recess and the hub. The rigidifying seal is not necessarily fluid tight but is configured to provide a rigidifying structure, and to prevent movement of the first and second fluid tight seals.

In an alternate embodiment of the adapter, the tapered post on the receptacle is removed, such that an enlarged opening is provided on the first medical instrument. In addition, the second medical instrument, and the fitting on the adapter, are provided with internal conduits having diameters matching that of the enlarged opening. The alternate embodiment adapter also includes a housing having a recess configured to slip over, or alternately to cut threads on the outside diameter of the hub of the receptacle. The enlarged opening permits fluids, tissue and cells to be transferred through the receptacle with less resistance and less damage.

The method for attaching the medical instrument to the receptacle includes the step of providing the adapter with the housing, the fitting, and the second medical instrument as described above. The method also includes the steps of slipping (or alternately threading) the recess in the housing to the outside diameter of the hub on the adapter, and slipping the tapered post on the receptacle into the tapered recess in the fitting. In addition, the method includes the step of twisting the housing to threadably engage the threads (or the flange) on the male end portion of the fitting with the female threads on the hub.

BRIEF DESCRIPTION OF THE DRAWINGS

FIG. 1A is a side elevation view of a prior art syringe;

FIG. 1B is an end view of the prior art syringe;

FIG. 1C is an enlarged cross sectional view taken along section line 1C—1C of FIG. 1A illustrating a prior art "LUER LOK" receptacle on the prior art syringe;

FIG. 1D is a side elevation view of a prior art cannula configured for attachment to the prior art "LUER LOK" receptacle;

FIG. 1E is an end view of the prior art cannula;

FIG. 1F is an enlarged cross sectional view illustrating the connection between the prior art cannula and the prior art "LUER LOK" receptacle;

DETAILED DESCRIPTION OF THE PREFERRED EMBODIMENTS

Referring to FIGS. 2A–2D, an adapter 40 constructed in accordance with the invention is illustrated. The adapter 40 includes a housing 42, a fitting 44 attached to the housing 42, and a medical instrument 46 attached to the fitting 44.

Figure 2B:
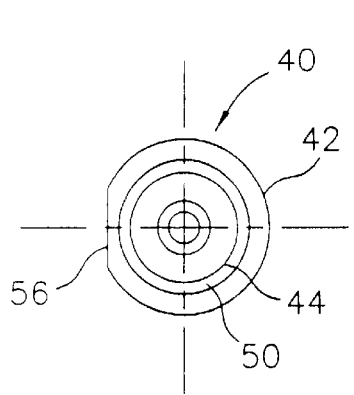
FIG. 2B is an end view of FIG. 2A.
Figure 2A:
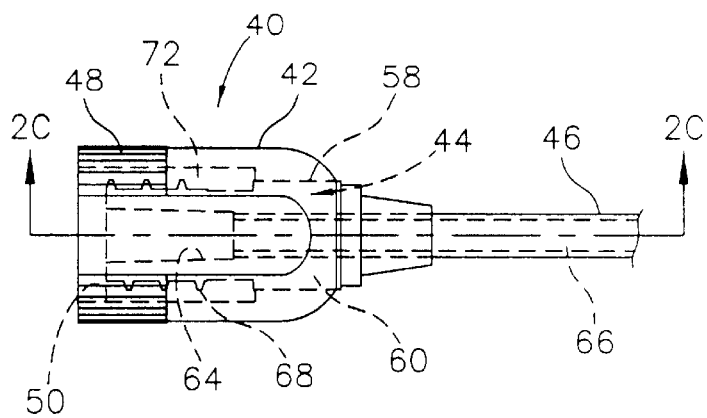
FIG. 2A is an enlarged side elevation view of an adapter constructed in accordance with the invention.

As shown in FIG. 2B, the housing 42 is generally cylindrical in shape, and includes a flat surface 56 which facilitates handling of the adapter 40. The housing 42 also includes a serrated or threaded surface 48 (FIG. 2A) which facilitates handling of the adapter 40, or attachment to a second adapter, such as the adapter disclosed in U.S. Pat. No. 5,002,538 to Johnson, which is incorporated herein by reference. The housing 42 can comprise a rigid material such as metal, hard plastic or a composite. An outside surface of the housing 42, other than the serrated or threaded surface 48, is preferably smooth or polished. In addition, the housing 42 can be molded, machined or otherwise formed with required features and dimensions.

Figure 2C:
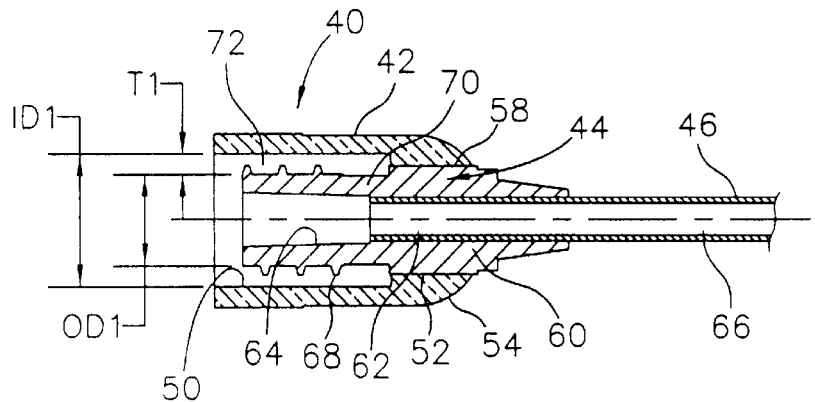
FIG. 2C is a cross sectional view taken along section line 2C—2C of FIG. 2A.

As shown in FIG. 2C, the housing 42 includes a cylindrical recess 50 having an inside diameter ID1 that is slightly larger (e.g., one to several mils) than the outside diameter OD (FIG. 1C) of the hub 18 on the receptacle 12. The recess 50 is configured to slip onto the hub 18 and to provide a press fit therebetween. This press fit is termed herein as a rigidifying seal. The housing 42 also includes an opening 52 for the medical instrument 46.

As also shown in FIG. 2C, the fitting 44 is attached to the housing 42, and to the medical instrument 46. Preferably the fitting 44 comprises a corrosion resistant metal such as stainless steel. The fitting 44 includes an annular shoulder 58 sized to be press fitted, or merely retained in the recess 50 in the housing 42. The fitting 44 also includes a tapered end portion 60 attached to the medical instrument 46, using a suitable attachment process such as welding, brazing or press fitting. Alternately, the fitting 44 and the medical instrument 46 can be machined or molded from a same piece of metal.

As also shown in FIG. 2C, the fitting 44 also includes an internal conduit 62 in flow communication with the inside diameter of the medical instrument 46. In addition, the fitting 44 includes a male end portion 70 having a tapered recess 64 in flow communication with the internal conduit 62. The tapered recess 64 is configured to be press fitted to the tapered post 22 (FIG. 2D) on the receptacle 12. With the tapered recess 64 press fitted to the tapered post 22 a fluid tight seal is formed therebetween. In addition, the inside of the barrel 14 of the syringe 10 is in flow communication with the internal conduit 62 in the fitting 44 and the inside diameter of the medical tool 46.

As also shown in FIG. 2C, the male end portion 70 of the fitting 44 has an outside diameter OD1 with male threads 68. The male threads 68 are configured to threadably engage the female threads 20 (FIG. 2D) on the hub 18 of the receptacle 12. In addition, the outside diameter OD1 of the male end portion 70 is sized such that an annular recess 72 is formed between the inside diameter ID1 of the recess 50 in the housing 42 and the outside diameter OD1 of the male end portion 70. This annular recess 72 has a thickness T1 that is about the same as, or slightly less than, a wall thickness T (FIG. 1C) of the hub 18 of the receptacle 12.

The medical instrument 46 can comprise any conventional instrument, such as a cannula configured to extract tissue from a patient, or a needle configured to inject a solution into a patient. The medical instrument 46 preferably comprises a metal such as stainless steel, and includes an inside diameter 66 in flow communication with the internal conduit 62 in the fitting 44 and with the inside of the barrel 14 of the syringe 10.

Figure 2D:
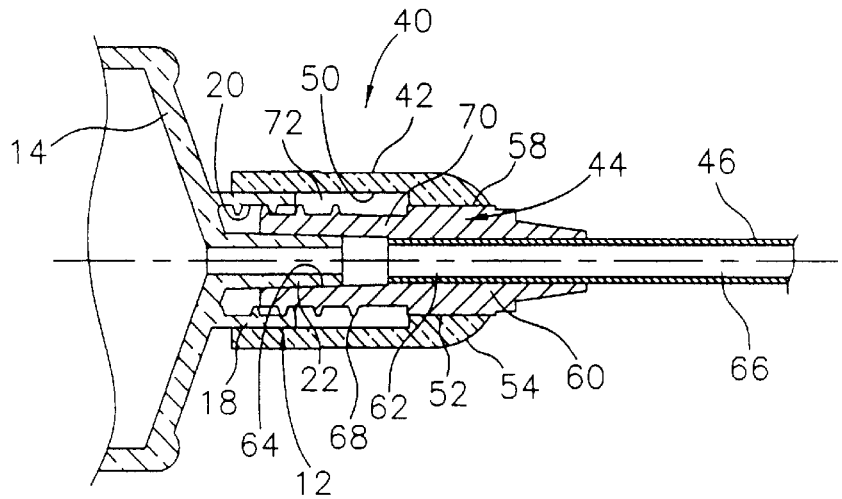
FIG. 2D is a cross sectional view of the adapter connected to a "LUER LOK" receptacle.

Referring to FIG. 2D, the adapter 40 is shown attached to the receptacle 12. For attaching the adapter 40 to the receptacle 12 the recess 50 is aligned and pressed onto the hub 18 of the receptacle. In addition, the tapered post 22 on the receptacle is aligned and pressed into the tapered recess 64 in male end portion 70 of the fitting 44. Further, the male threads 68 on male end portion 70 of the fitting 44 are aligned with the female threads 20 on the hub 18 of the receptacle 12. The housing 42 of the adapter 40 is then twisted in a clockwise direction to threadably engage, or lock, the male threads 68 to the female threads 20. With the threads 68, 20 engaged, a first fluid tight seal is formed between the threads 68, 20. The action of the threads 68, 20 also pulls the tapered recess 64 onto the tapered post 22 such that a second fluid tight seal is formed. In addition, the action of the threads 68, 20 pulls the recess 50 into a press fit with the hub 18 such that the rigidifying seal is formed. The rigidifying seal also helps to protect and maintain the first and second fluid tight seals. However, as will be further explained, this rigidifying seal can also be made fluid tight with the addition of threads, or a taper portion on the recess 50.

In addition to forming the rigidifying seal, the recess 50 supports the entire outside diameter of the hub 18 and prevents the hub 18 from spreading. This rigidified structure allows the medical instrument 46 to be manipulated more aggressively, and decreases the likelihood of the hub 18 or other elements of the receptacle 12 from cracking or breaking. The rigidified structure also protects the fluid tight seals from movement and damage, and helps to prevent fluids, vacuum or pressure from leaking through the fluid tight seals.

Figure 2E:
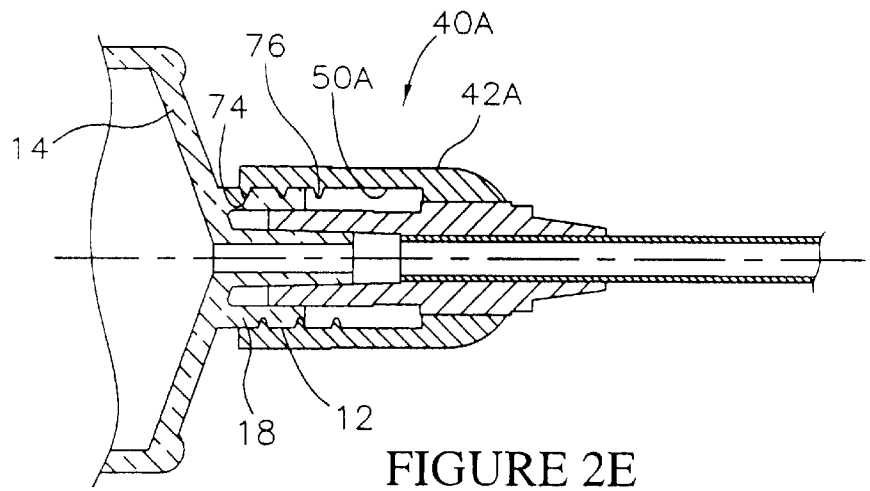
FIG. 2E is a cross sectional view equivalent to FIG. 2D of an alternate embodiment adapter configured to cut threads in a hub of a "LUER LOK" receptacle.

Referring to FIG. 2E, an alternate embodiment adapter 40A is illustrated. The adapter 40A is constructed substantially as previously described for adapter 40. However, in this embodiment a housing 42A of the adapter 40A includes a recess 50A having cutting threads 74 configured to cut mating threads 76 on the hub 18 of the receptacle 12. The press fit provided by the recess 50 in the housing 42 is thus replaced by a fluid tight thread fit. In addition, the threads 74, 76 help to rigidify and strengthen the hub 18 substantially as previously described.

Figure 2F:
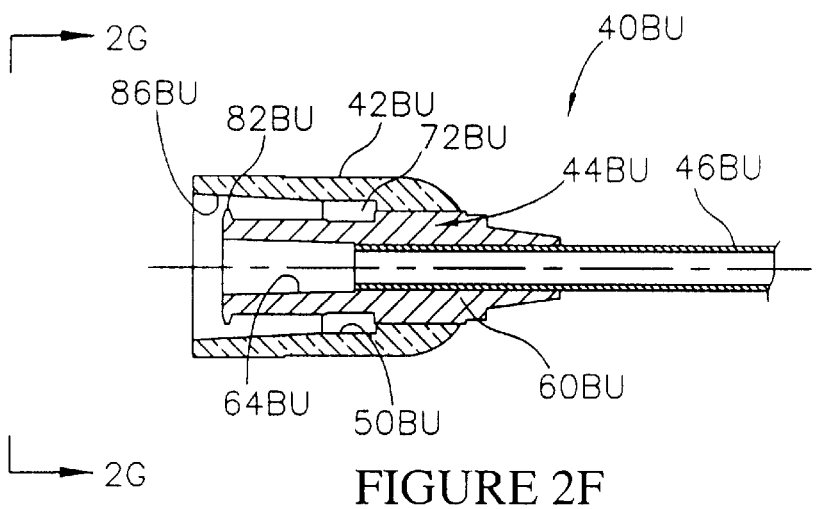
FIG. 2F is a cross sectional view equivalent to FIG. 2C of an alternate embodiment butterfly adapter having a flange rather than male threads.
Figure 2G:
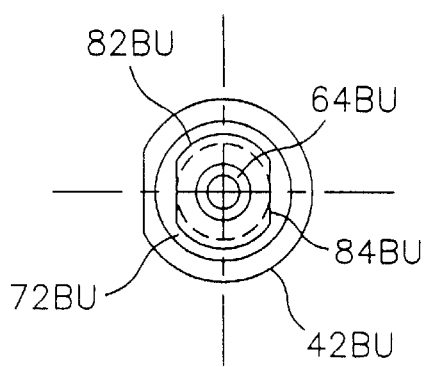
FIG. 2G is an end view taken along line 2G—2G of FIG. 2F showing the flange on the butterfly adapter.
Figure 2H:
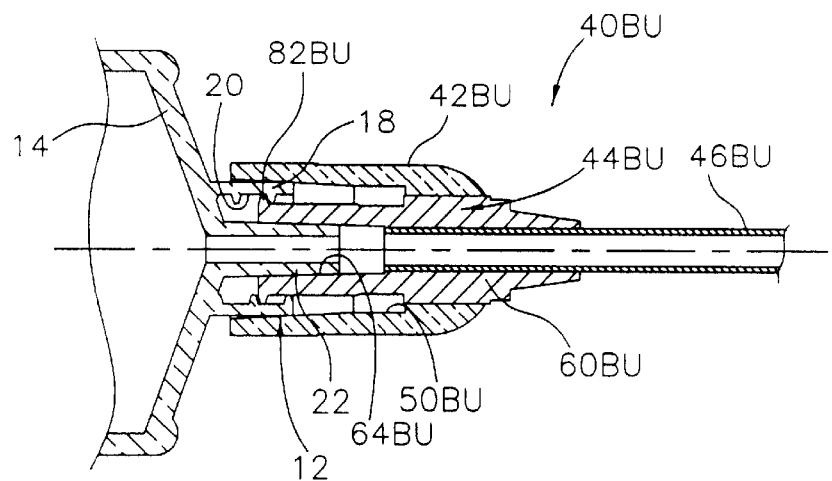
FIG. 2H is a cross sectional view equivalent to FIG. 2D of the butterfly adapter connected to the "LUER LOK" receptacle.

Referring to FIGS. 2F–2H an alternate embodiment butterfly adapter 40BU is illustrated. The butterfly adapter 40BU is constructed substantially as previously described for adapter 40 (FIG. 2C) but with a flange 82BU rather than threads 68 (FIG. 2C).

The butterfly adapter 40BU includes a housing 42BU, and a fitting 44BU attached to the housing 42BU. The butterfly adapter 40BU also includes a medical instrument 46BU attached to the housing 42BU. In addition, the housing 42BU includes a recess 50BU configured to form a rigidifying seal with a hub 18 (FIG. 2H) of the receptacle 12 (FIG. 2H) substantially as previously described. The recess 50BU includes a tapered portion 86BU (or chamfer) which is configured to make the rigidifying seal fluid tight.

The fitting 44BU includes a male end portion 60BU configured to form an annular recess 50BU substantially as previously described. The male end portion 60BU includes a flange 82BU which is configured to threadably engage the threaded inside diameter 20 (FIG. 2H) of the receptacle 12 (FIG. 2H). As shown in FIG. 2G, the flange 82BU is not continuous, but includes flats 84BU, such that engagement with the threaded inside diameter 20 is facilitated. The male end portion 60BU of the fitting 44BU also includes a tapered recess 64BU configured to form a fluid tight seal with the tapered post 22 (FIG. 2H) of the receptacle 12 (FIG. 2H) substantially as previously described.

Figures 3A, 3B:
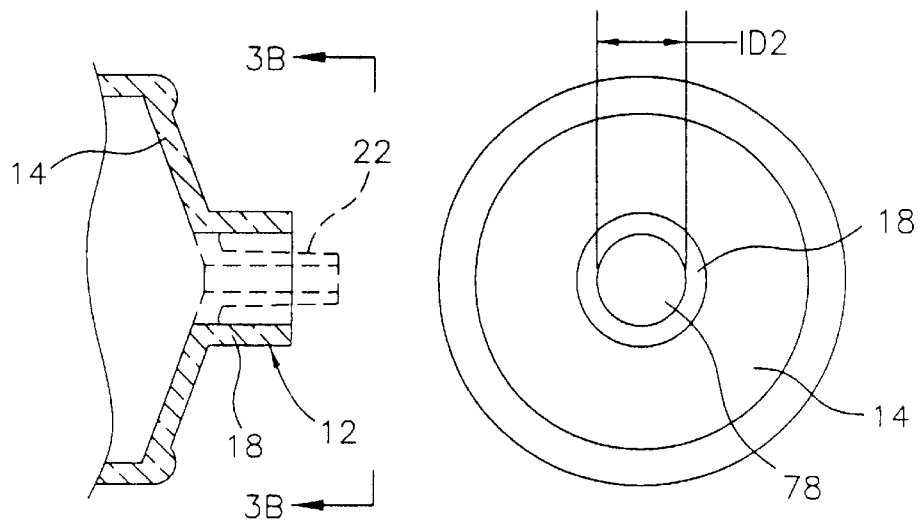
FIG. 3A is a side elevation view of a "LUER LOK" receptacle that has been modified to remove a tapered post component and form a larger opening for the receptacle.
FIG. 3B is an end view of FIG. 3A.
Figure 3C:
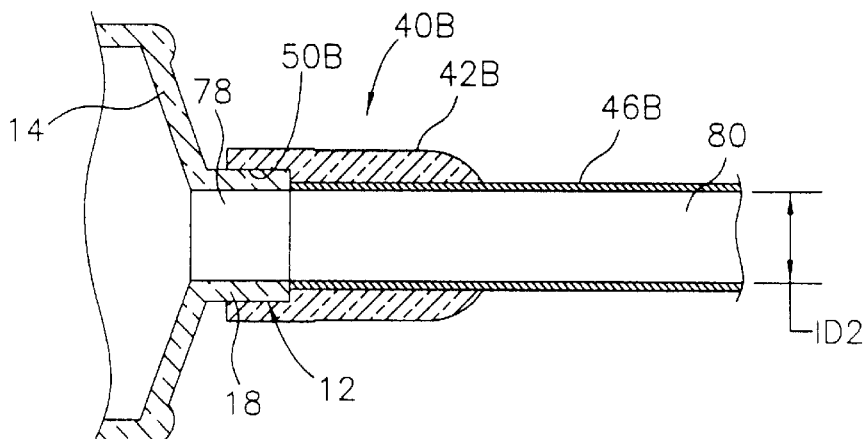
FIG. 3C is a cross sectional view equivalent to FIG. 2D of an alternate embodiment adapter attached to the modified "LUER LOK" receptacle.

Referring to FIGS. 3A–3C, an alternate embodiment adapter 40B (FIG. 3C) is illustrated. As shown in FIG. 3A, to utilize the adapter 40B the tapered post 22 of the receptacle 12 is removed. Removal of the tapered post 22 can be accomplished using a razor, an "EXACTO" knife or a tool specially constructed to remove the tapered post 22. As shown in FIG. 3B, removing the tapered post 22 forms an enlarged opening 78 in the barrel 14 of the syringe 10. This enlarged opening has an inside diameter ID2 of about 6.3 mm–6.5 mm, which is about three times larger than the inside diameter ID (FIG. 1C) of the tapered post 22.

As shown in FIG. 3C, the adapter 40B includes a housing 42B having a cylindrical recess 50B configured to press fit over the outside diameter of the hub 18 of the receptacle 12. As with the previous embodiments, the adapter 40B provides a rigidifying structure, and the press fit provides a rigidifying seal. Alternately the recess 50B can be configured to cut threads substantially as previously described for adapter 40A (FIG. 2E) or can include a tapered portion 86BU such that a fluid tight seal is formed.

The adapter 40B also includes a medical instrument 46B attached to the housing 40B substantially as previously described for medical instrument 46. However, the instrument 46B has an inside diameter that matches the inside diameter ID2 of the enlarged opening 78. The enlarged opening 78 permits increased volumes of fluids, and/or body tissue, such as harvested cells, to be passed through the medical instrument 46B with less resistance, such that less effort is required for medical technicians. In addition, the enlarged opening allows fluids to be transferred with less damage to the fluid. This is of particular importance to fluids containing cells harvested from the body.

Thus the invention provides an adapter for "LUER LOK" receptacles, and a method for attaching medical instruments to "LUER LOK" receptacles. Although the invention has been described with reference to certain preferred embodiments, as will be apparent to those skilled in the art, certain changes and modifications can be made without departing from the scope of the invention as defined by the following claims.

We claim:

1. An adapter for a medical receptacle having a hub with an outside diameter and a threaded inside diameter, and a tapered post within the hub, the adapter comprising:
    a housing comprising a recess configured to encircle, seal and rigidify the outside diameter of the hub of the receptacle; and
    a fitting attached to the housing comprising an internal conduit, a tapered recess aligned with the internal conduit configured to engage the tapered post, and a male end portion configured to engage the threaded inside diameter of the hub of the receptacle.

2. The adapter of claim 1 wherein the medical receptacle comprises a syringe.

3. The adapter of claim 1 wherein the male end portion comprises a flange configured to threadably engage the threaded inside diameter.

4. The adapter of claim 1 further comprising a medical instrument attached to the housing in flow communication with the internal conduit.

5. The adapter of claim 1 wherein the recess is configured to press fit to the outside diameter of the hub of the receptacle.

6. The adapter of claim 1 wherein the recess comprises cutting threads configured to cut mating threads on the outside diameter of the hub of the receptacle.

7. The adapter of claim 1 wherein the recess comprises a tapered portion and is configured to form a fluid tight seal with the outside diameter of the hub of the receptacle.

8. An adapter for a medical receptacle having a hub with an outside diameter and a threaded inside diameter, and a tapered post within the hub, the adapter comprising:
    a housing comprising a recess configured to encircle the outside diameter of the hub of the receptacle, to rigidify the hub of the receptacle, and to prevent the hub of the receptacle from spreading; and
    a fitting attached to the housing comprising a portion within the recess having a plurality of male threads configured to engage the threaded inside diameter of the hub of the receptacle, a tapered recess in the portion configured to engage the tapered post, and an internal conduit extending from the tapered recess.

9. The adapter of claim 8 further comprising a medical instrument attached to the housing in flow communication with the internal conduit.

10. The adapter of claim 8 further comprising a cannula or a needle attached to the housing in flow communication with the internal conduit.

11. The adapter of claim 8 wherein the medical receptacle comprises a syringe.

12. The adapter of claim 8 wherein the recess is configured to thread to the outside diameter of the hub of the receptacle.

13. The adapter of claim 8 wherein the recess is configured to form a fluid tight seal with the outside diameter of the hub of the receptacle.

14. An adapter for a medical receptacle having a hub with female threads and a tapered post within the hub having an internal opening, the adapter comprising:
    a housing comprising a recess configured to encircle the hub of the receptacle to form a rigidifying seal; and
    a fitting attached to the housing having a first portion within the recess and a second portion extending from the housing,
    the fitting comprising a plurality of male threads on an outside surface of the first portion configured to engage the female threads on the hub of the receptacle to form a first fluid tight seal, a tapered recess in the first portion configured to engage the tapered post to form a second fluid tight seal, and an internal conduit extending through the first portion and the second portion configured for flow communication with the internal opening in the tapered post,
    the rigidifying seal configured to prevent movement of the first fluid tight seal and the second fluid tight seal.

15. The adapter of claim 14 further comprising a medical instrument attached to the second portion of the fitting having an inside diameter in flow communication with the internal conduit.

16. The adapter of claim 14 wherein the recess is configured to form a press fit with an outside diameter of the hub of the receptacle and to rigidify and prevent the hub from spreading.

17. The adapter of claim 14 wherein the recess comprises a plurality of threads configured to cut mating threads on an outside diameter of the hub of the receptacle.

18. The adapter of claim 14 wherein the recess comprises a tapered portion configured to form a fluid tight seal with an outside diameter of the hub of the receptacle.

19. The adapter of claim 14 wherein the fitting is configured to form an annular recess in the recess having a thickness approximately equal to a wall thickness of the hub of the receptacle.

20. An adapter for a medical receptacle having a hub with female threads and a tapered post within the hub having an internal opening, the adapter comprising:
    a housing comprising a recess configured to encircle, seal and rigidify the hub of the receptacle; and
    a fitting attached to the housing having a first portion within the recess and a second portion extending from the housing,
    the fitting comprising at least one flange on an outside surface of the first portion configured to engage the female threads on the hub of the receptacle, a tapered recess in the first portion configured to engage the tapered post to form a fluid tight seal, and an internal conduit extending through the first portion and the second portion configured for flow communication with the internal opening in the tapered post.

21. The adapter of claim 20 wherein the recess comprises a tapered portion and is configured to form a second fluid tight seal with the hub of the receptacle.

22. In a medical receptacle having a hub with an outside diameter and a threaded inside diameter, and a tapered post within the hub, a method for attaching a medical instrument to the receptacle comprising:

providing an adapter comprising:
a housing comprising a recess configured to encircle, seal and rigidify the outside diameter of the hub; and
a fitting attached to the housing comprising a first portion within the recess having a male end portion configured to engage the threaded inside diameter of the hub, a tapered recess in the male end portion configured to engage the tapered post, a second portion attached to the medical instrument, and an internal conduit in flow communication with the medical instrument;

engaging the outside diameter of the hub with the recess;
engaging the tapered post with the tapered recess; and
twisting the housing to engage the male end portion on the fitting to the threaded inside diameter of the hub.

23. The method of claim 22 wherein the male end portion comprises a plurality of threads.

24. The method of claim 22 wherein the male end portion comprises at least one flange.

25. The method of claim 22 wherein the engaging the outside diameter step comprises press fitting the recess to the outside diameter of the hub.

26. The method of claim 22 wherein the engaging the outside diameter step comprises threading the recess to the outside diameter of the hub.

27. In a medical receptacle having a hub with an outside diameter and a threaded inside diameter, and a tapered post within the hub, a method for attaching a medical instrument to the receptacle comprising:

removing the tapered post to form an enlarged opening;
providing an adapter attached to the instrument, the adapter comprising a recess configured to encircle, seal and rigidify the outside diameter of the hub; and
engaging the outside diameter of the hub with the recess.

28. The method of claim 27 wherein the engaging step comprises press fitting the recess to the outside diameter of the hub.

29. The method of claim 27 wherein the engaging step comprises providing the recess with cutting threads and then forming mating threads on the outside diameter of the hub using the cutting threads.

30. The method of claim 27 wherein the engaging step comprises providing the recess with a tapered portion and then forming a fluid tight seal with the outside diameter of the hub using the tapered portion.

* * * * *